(12) United States Patent
Hirasawa et al.

(10) Patent No.: US 8,222,622 B2
(45) Date of Patent: Jul. 17, 2012

(54) ELECTRON IRRADIATION APPARATUS OF DC-TYPE DIELECTRIC BARRIER DISCHARGE AND ELECTRICAL THERAPEUTIC APPARATUS

(75) Inventors: Keisuke Hirasawa, Hachioji (JP); Masaharu Dozen, Tokyo (JP); Yuki Tada, Tokyo (JP); Daijiro Okihara, Hadano (JP)

(73) Assignee: Cambwick Healthcare K.K., Tokyo (JP)

( * ) Notice: Subject to any disclaimer, the term of this patent is extended or adjusted under 35 U.S.C. 154(b) by 0 days.

(21) Appl. No.: 13/055,120

(22) PCT Filed: Aug. 4, 2009

(86) PCT No.: PCT/JP2009/003714
§ 371 (c)(1),
(2), (4) Date: Mar. 24, 2011

(87) PCT Pub. No.: WO2010/016238
PCT Pub. Date: Feb. 11, 2010

(65) Prior Publication Data
US 2011/0180732 A1 Jul. 28, 2011

(51) Int. Cl.
*A61N 5/10* (2006.01)
(52) U.S. Cl. ............... 250/492.3; 313/334
(58) Field of Classification Search ............ 250/492.1, 250/492.3, 428, 432 R; 313/311, 325, 334
See application file for complete search history.

(56) References Cited

U.S. PATENT DOCUMENTS

| | | | | |
|---|---|---|---|---|
| 4,092,559 A | * | 5/1978 | Dashuk | 307/108 |
| 6,475,350 B2 | * | 11/2002 | Palekar et al. | 204/164 |
| 7,956,547 B2 | * | 6/2011 | Maeda et al. | 315/205 |
| 2001/0001435 A1 | * | 5/2001 | Palekar et al. | 204/164 |
| 2004/0222082 A1 | * | 11/2004 | Gopalraja et al. | 204/192.3 |
| 2005/0143726 A1 | * | 6/2005 | Bortkiewicz | 606/41 |
| 2011/0171626 A1 | * | 7/2011 | Hirasawa et al. | 435/1.2 |
| 2011/0240888 A1 | * | 10/2011 | Rosenzweig et al. | 250/492.3 |
| 2011/0297844 A1 | * | 12/2011 | Vecziedins et al. | 250/432 R |

FOREIGN PATENT DOCUMENTS

| | | |
|---|---|---|
| JP | 11-276602 | 10/1999 |
| JP | 2001-309987 | 11/2001 |
| JP | 2005-296441 | 10/2005 |
| JP | 2006-324128 | 11/2006 |
| JP | 2007-042323 | 2/2007 |
| WO | 2006/116252 | 11/2006 |

* cited by examiner

Primary Examiner — Bernard E Souw

(57) ABSTRACT

A DC power supply 1 is connected with the DC-type high voltage generator 2 that boosts the power supply. A negative output terminal 3 and a positive output terminal 6 of the generator 2 are respectively connected to a cathode electrode 5 and an anode electrode 7. A dielectric sheet 4 with appropriate relative permittivity and certain range of volume resistivity is closely attached on the cathode electrode surface opposed to the anode electrode. The cathode electrode 5 together with the dielectric sheet 4 constitutes a DC-type dielectric barrier electrode 9. The power supply 1 and the generator 2 are disposed on an upper surface of a belt-type attachment 15, and the discharge electrode 9 and the anode electrode 7 are disposed on the lower surface thereof. The electrodes 9 and 7 become opposed to each other upon wrapping the attachment 15 around the affected part of a subject.

8 Claims, 9 Drawing Sheets

FIG. 1

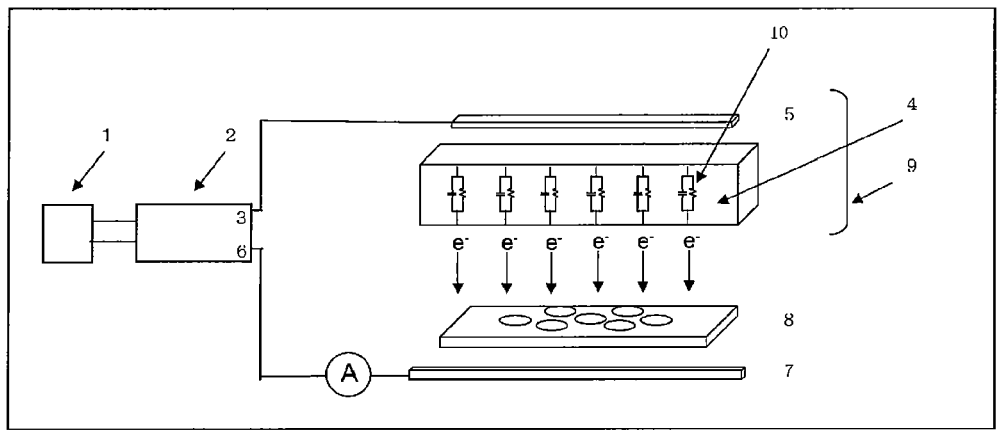

FIG. 2

| Dielectric material | Electric current (μA) |
|---|---|
| Polyurethane rubber A (2-mm thick) | 9.93 |
| Polyurethane rubber B (1-mm thick) | 1.52 |
| Polyurethane rubber C (2-mm thick) | 1.08 |
| Chloroprene rubber (1-mm thick) | 4.01 |
| Chloroprene rubber (2-mm thick) | 0.85 |
| Chloroprene rubber (3-mm thick) | 0.57 |
| Nitrile rubber (3-mm thick) | 8.25 |
| Nitrile rubber (containing carbon, 3-mm thick) | 28.77 |
| Butyl rubber (containing carbon, 1-mm thick) | 36.10 |
| Vinyl chloride sheet (0.3-mm thick) | 0.58 |
| Silicon rubber (2-mm thick) | 0.27 |

| Dielectric material | Volume resistivity (Ωcm) | Relative permittivity (ε) |
|---|---|---|
| Polyurethane rubber A | 5.6E+09 | 8.5 |
| Polyurethane rubber B | 6.3E+11 | 5.9 |
| Polyurethane rubber C | 8.6E+13 | 5.1 |
| Chloroprene rubber | 3.0E+12 | 14.1 |
| Nitrile rubber (3-mm thick) | 2.6E+10 | 30 |
| Nitrile rubber (containing carbon) | 1.1E+07 | 330 |
| Vinyl chloride sheet | 5.1E+12 | 3.7 |
| Silicon rubber | 4.5E+13 | 4.4 |

The relative permittivity is measured at 1 kHz.

Electric current when a cathode electrode of the size of 10mm × 70mm is used

| Shielded part | (1) | (2) | (3) | (4) |
|---|---|---|---|---|
| Distance from the electrode (cm) | - | 0 | 1 | 2 |
| Electric current (μA) | 0.25 | 3.54 | 5.90 | 6.42 |
| Electric current of the portion where slit are newly extended | - | 3.29 | 2.36 | 0.52 |
| Electric current per unit area (μA/cm$^2$) | - | 0.37 | 0.13 | 0.03 |

Electric current when using cathode electrode having the same size as a dielectric material

| Shielded part | (1) | (2) | (3) | (4) |
|---|---|---|---|---|
| Distance from the electrode (cm) | - | 0 | 0 | 0 |
| Electric current (μA) | 0.32 | 2.25 | 5.02 | 8.08 |
| Electric current of the portion where slit are newly extended | - | 1.93 | 2.77 | 3.06 |
| Electric current per unit area (μA/cm$^2$) | - | 0.21 | 0.15 | 0.17 |

US 8,222,622 B2

ELECTRON IRRADIATION APPARATUS OF DC-TYPE DIELECTRIC BARRIER DISCHARGE AND ELECTRICAL THERAPEUTIC APPARATUS

TECHNICAL FIELD

The present invention relates to an electron irradiation apparatus which realizes the use of DC high voltage power supply together with a plate electrode using dielectric material, from which surface electron is discharged and irradiated to an object so that a minor electric current flows within the irradiated material, and also relates to an electrical therapeutic apparatus equipped with such electron irradiation apparatus.

BACKGROUND ART

Electric discharge phenomena are in general dielectric breakdown observed in the DC circuit, and are known as a spark discharge or a corona discharge that involves emission of sounds. In these discharges, the current is converged so as to cause damages to the irradiated object, since the current density is high even when the discharged current is minor. Such discharge phenomena with the converged current are industrially utilized for automobile spark plug, etc.

Also, in the medical field, there is an electrical therapeutic apparatus utilizing a DC-type corona discharge which applies a certain level of electric current to the human body. For example, Patent Documents 1-3 disclose the technology utilizing the said DC-type corona discharge.

In addition, there is an electrical therapeutic apparatus utilizing a disruptive discharge of dielectric in the AC high voltage circuit. That is, the dielectric barrier discharge (silent discharge) is known as means for to causing planar discharge of electron in prevention of converging high electric current. In this electric discharge method, AC voltage is applied to the electrode containing dielectric material to discharge electron. For example, Patent Document 4 discloses a technology using the AC-type dielectric barrier discharge.

In industrial applications, an apparatus for producing ozone is widely used in which AC voltage is applied to dielectric electrodes arranged with a certain gap therebetween so that electron is discharged alternately from the electrodes. In addition, Patent Document 5 discloses the technology of AC-type dielectric barrier discharge.

Patent document 1: Japanese Patent Application Laid-open No. 2001-309987
Patent document 2: Japanese Patent No. 4024227
Patent document 3: Japanese Patent Application Laid-open No. 2007-42323
Patent document 4: Japanese Patent Application Laid-open No. 11-276602
Patent document 5: Japanese Patent Application Laid-open No. 2006-324128

DISCLOSURE OF THE INVENTION

However, since the conventional method of dielectric barrier discharge is of AC type where the positive/negative polarity is alternated, the electric current produced by the discharge flows bidirectionally due to the applied AC voltage. This is not acceptable for the purpose of unidirectional and constant amount of electron discharge.

In particular, the above electric discharge method, when applied to a medical device for therapeutic purpose, alternately causes provision and deprivation of electrons to and from the human body being treated. This is not suitable for precisely controlling the amount of applied electron.

The inventors made efforts, while maintaining the planar discharge that is the feature of conventionally-known AC-type dielectric barrier discharge, to achieve unidirectional electron discharge in a new DC-type dielectric barrier discharge.

However, in realization of such an improvement, there was a major hurdle. That is, as known conventionally, in application of DC voltage, the dielectric barrier discharge should be consisting of lots of minor discharges at various spots independent to each other, however, once a discharge occurs at one spot, the electric potential in that spot decreases and a subsequent discharge is terminated so that sequential discharge on the plane will not occur.

The inventors, through intensive investigation for realizing a DC-type dielectric barrier discharge that had been considered impossible and for which no known embodiment is available, finally completed to achieve the new method of DC-type dielectric barrier discharge.

In order to achieve the above object, the present invention provides an electron irradiation apparatus, in which a negative output terminal of a DC-type high voltage power supply is connected with a cathode electrode, a positive output terminal of the DC-type high voltage power supply is connected with an anode electrode, a dielectric material is closely attached to a surface of the cathode electrode facing the anode electrode, and the cathode electrode and the dielectric material constitute a dielectric barrier discharge electrode, wherein electrons are discharged unidirectionally from a surface of the dielectric material by applying a DC high voltage between the dielectric discharge electrode and the anode electrode.

In another aspect of the present invention, the dielectric material is made of a substance of which volume resistivity is $10^{13}$ $\Omega\cdot cm$ or less and relative permittivity is 5 or more, and the dielectric material is formed by mixing a raw dielectric material with a conductive substance such that the volume resistivity is decreased and the relative permittivity is increased.

The present invention also provides an electrical therapeutic apparatus equipped with said electron irradiation apparatus, wherein a region to be irradiated is arranged between the dielectric discharge electrode and the anode electrode of the electron irradiation apparatus. In addition, the said electron irradiation apparatus can be equipped with a current controlling circuit to adjust a maximum current flowing between the electrodes at a pre-set current value.

The electron irradiation apparatus of the present invention, having the above structure, achieves uniform and unidirectional flows of electrons constantly produced from the whole area of the dielectric discharge electrode. Furthermore, the electrical therapeutic apparatus incorporating the electron irradiation apparatus achieves safe and high therapeutic effect by virtue of the uniform irradiation of electron appropriately flowed in over the whole area to be treated.

BRIEF DESCRIPTION OF THE DRAWINGS

FIG. 1 is a wiring diagram showing a first embodiment of the invention.

FIG. 2 is a table showing a result of measuring the discharged electric currents when various dielectric materials are used according to the first embodiment.

EXPLANATION OF REFERENCE NUMERALS

Figures 3, 4:
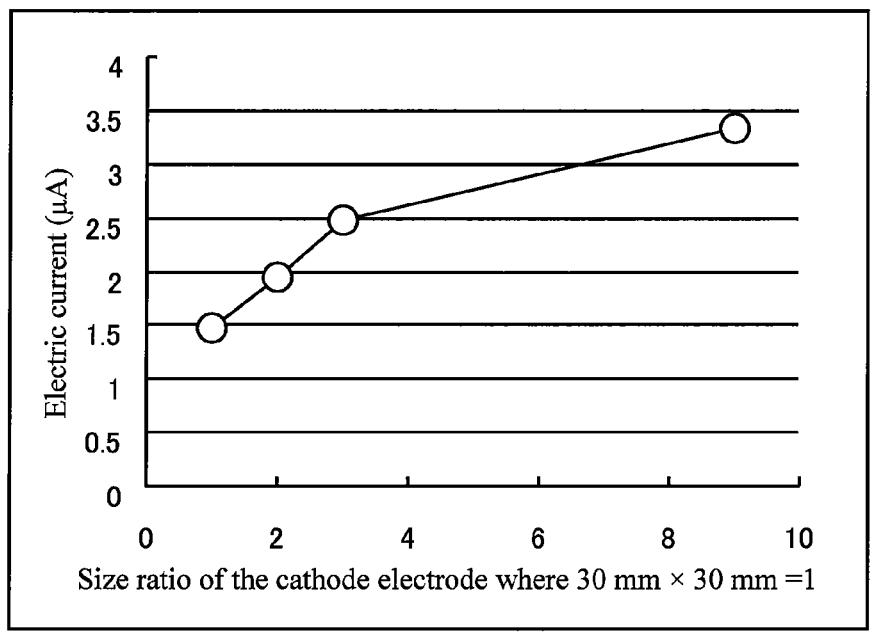
FIG. 3 is a table showing the relative permittivity and volume resistivity of the dielectric material used in the invention.
FIG. 4 is a graph showing the amount of the discharged electric current corresponding to the size of the cathode electrode attached to dielectric material according to a second embodiment of this invention.

1 . . . DC power supply
2 . . . DC-type high voltage generator
3 . . . Negative output terminal
4 . . . Dielectric material sheet
5 . . . Cathode electrode
6 . . . Positive output terminal
7 . . . Anode electrode
8 . . . Acrylic plate
9 . . . DC-type dielectric barrier discharge electrode
10 . . . Parameter elements equally distributed in dielectric material
11 . . . Polymer gel
12 . . . Arm (human body)
13 . . . Insulation cloth
14 . . . Connecting wire
15 . . . Belt-type attachment
16 . . . Conductive wire for discharge electrode
17 . . . Conductive wire for anode electrode
18 . . . Variable voltage supply circuit
19 . . . High voltage rectifier circuit
20 . . . Feedback controlling circuit
21, 22 . . . Input terminals of variable voltage supply circuit
23, 24 . . . Output terminals of variable voltage supply circuit
25 . . . Input terminal of controlling variable voltage supply
26, 27 . . . Input terminals of high voltage rectifier circuit
28, 29 . . . Output terminals of high voltage rectifier circuit
30, 31 . . . Input terminals of feedback controlling circuit
32 . . . Output terminal of feedback controlling circuit
33 . . . Resistor

BEST MODE FOR CARRYING OUT THE INVENTION (First Embodiment)

In the following, a first embodiment of the present invention is explained in detail in reference to FIGS. 1-4. FIG. 1 is a wiring diagram showing the circuit configuration according to the first embodiment. In this circuit, as one example, a DC power supply 1 using a dry battery of 6 volts is connected with a DC high voltage generator 2, which boosts the 6 volts to minus 5500 volts. A negative output terminal 3 of the DC high voltage generator 2 is connected with a metal cathode electrode 5, and a positive output terminal 6 of the DC high voltage power supply 2 is connected with an anode electrode 7. A dielectric material sheet 4, which has an appropriate relative permittivity and a certain range of volume resistivity, is closely attached on a surface of the metal cathode electrode 5 that is opposed to the anode electrode 7. In the first embodiment, a 2-mm-thick polyurethane rubber sheet is used as the dielectric material sheet 4. That is, according to the first embodiment, the DC-type dielectric barrier discharge electrode 9 is constituted by closely attaching the cathode electrode 5 to the dielectric material sheet 4.

Next, the operation of the electron irradiation apparatus of the first embodiment constituted as mentioned above is explained. As an object to be irradiated with the electron, an insulative acrylic plate 8 with through-holes (air vents) is placed between the dielectric material sheet 4 attached to the cathode electrode 5 and the anode electrode 7. The acrylic plate 8 is of 2-mm thick. The anode electrode 7 is connected to the positive output terminal 6 of the DC high voltage power supply 2, and an ampere meter (indicated as "A" in the drawings) is placed therebetween.

In the same manner, an apparatus as a comparative example is prepared, which is composed by disposing the acrylic plate 8 of the same thickness between the cathode electrode 5 and the anode electrode 7, though without providing the dielectric material sheet 4. In the configuration of comparative example, when the voltage of minus 5500 volts is applied from the DC-type high voltage generator 2 to the acrylic plate 8 via the cathode electrode 5 and anode electrode 7, spark discharges continued with sparks and sounds are observed via the through-holes of the acrylic plate 8. The level of electric current irregularly varies in the range of 6 to 13 micro amperes.

On the other hand, according to the first embodiment using the DC-type dielectric barrier electrode 9 in which the dielectric material sheet 4 is closely attached to the cathode electrode 5, when a voltage of minus 5500 volts is applied from the DC-type high voltage generator 2 to the acrylic plate 8 via the cathode electrode 5 and the anode electrode 7, a silent discharge is continued stably with 9.93 micro amperes.

The above results indicate that, by selecting an appropriate dielectric material, the DC-type dielectric barrier discharge (silent discharge) where only the unidirectional discharge occurs under the DC voltage can be realized in a simple configuration only with the cathode electrode attached by a single layer of dielectric material, and the anode electrode.

The mechanism of DC-type dielectric barrier discharge is recognized as follows. That is, when lots of independent, minor discharges occur on the surface of dielectric material in various spots, as the applied voltage is direct current, usually once a discharge occurs, the electric potential on the surface spot of dielectric material is decreased and thus the discharge eventually ceases. However, when an appropriate volume resistivity of the dielectric material is selected, it is explained that the dielectric material itself electrically functions as a circuit with distributed constants where the capacitor and resistance are connected in parallel so as to develop minor discharges continually in various spots on the surface.

FIG. 2 shows the results of measuring the amount of discharged current when various dielectric materials are used as dielectric material sheet in the electron irradiation apparatus of the first embodiment. The measured values of FIG. 2 indicate that the amount of discharged current differs depending on the dielectric material used, for example, a 2-mm-thick polyurethane rubber, chloroprene rubber, or silicon rubber. In addition, from the comparison between polyurethane A and C, which have the same polyurethane structures though their molecular constructions being different with each other, it is discovered that the amount of discharged electron is influenced by the molecular construction specific to the urethane materials. Moreover, it becomes clear that, by increasing the thickness of dielectric material, the resistance is increased and thus the amount of discharged current is decreased.

Furthermore, when using carbon-containing insulative rubbers, which are nitrile rubber (3-mm-thickness) and butyl rubber (1-mm-thickness) respectively, the suitable amount of discharged electron can be achieved, that is, 28.77 micro amperes and 36.10 micro amperes respectively. However, in the case of butyl rubber, a spark discharge is observed and a dielectric barrier discharge can not be achieved since the property of conductive material is superior to that of dielectric material.

As seen from the above, the amount of discharged current can be increased by adding a conductive substance; however, it is essential to select a material while maintaining the property of the dielectric barrier discharge electrode. When the configuration of the first embodiment as shown in FIG. 1 is employed, it is necessary for the electron irradiation apparatus of the present invention that not a spark discharge but a silent discharge can be observed.

Then, in order to specify a proper condition of the dielectric material to be used, in addition to the amount of electric current shown in FIG. 2, the volume resistivity and relative permittivity of each dielectric material listed in FIG. 2 are measured. The results are shown in FIG. 3. FIG. 3 indicates that each dielectric material has its own volume resistivity and relative permittivity, which have influence over the amount of discharged current.

That is, it is shown that, by using the dielectric material having the insulation rate of which volume resistivity is $10^{13}$ $\Omega \cdot cm$ or less and the relative permittivity of 5 or more, the DC-type dielectric barrier discharge is easily achieved. As for examples of such dielectric material, there are polyurethane, chloroprene rubber, nitrile rubber, etc.

As for the dielectric material for the dielectric barrier discharge electrode, it is essential not to develop the spark discharge in the experiment in FIG. 1 as mentioned above. However, the materials for electrode are not to be limited to the listed examples but the material having equivalent properties are also available.

In addition, as seen from FIGS. 2 and 3, when 3-mm-thick nitrile rubber having the relative permittivity of 30 and volume resistivity of $2.6 \times 10^{10}$ $\Omega \cdot cm$ is used, the amount of discharged current is 8.25 micro amperes. In contrast, when conductive carbon powder is added to the nitrile rubber, decrease in volume resistivity and increase in relative permittivity are observed, and the amount of discharged current is increased to 28.77 micro amperes. This is because the added conductive substance influences the volume resistivity and relative permittivity of the dielectric material so as to accelerate the decrease of the volume resistivity and the recovery of electric potential due to electric current within the dielectric material, and thereby shortening the recovery time in the repeated cycle in which minor discharges are again generated, and the amount of discharged current is resultantly increased.

Moreover, the inventors have investigated the relationship between the amount of discharged current and the applied voltage in the DC-type dielectric barrier discharge. As a result, it has been found that, by increasing the voltage to be applied from the DC high voltage generator 2 to the dielectric material electrode 9, the amount of discharged current is increased in proportion to the applied volume. In this case, a necessary amount of discharged current is adjustable by controlling the amount of voltage.

(Second Embodiment)

Next, a second embodiment is explained, in which the relationship of the amount of discharged current with respect to the area and shape of the cathode electrode attached to the dielectric material is examined. As shown in FIG. 4, it is found that, by increasing and decreasing the area of cathode electrode attached to the dielectric material, under the constant voltage, the amount of discharged current is proportionally increased and decreased respectively.

Figure 5:
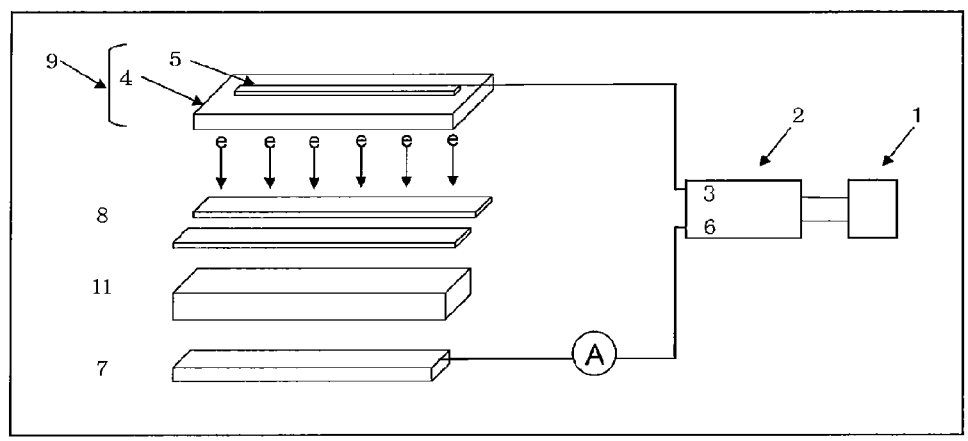
FIG. 5 is a wiring diagram showing the second embodiment of this invention.
Figure 6:
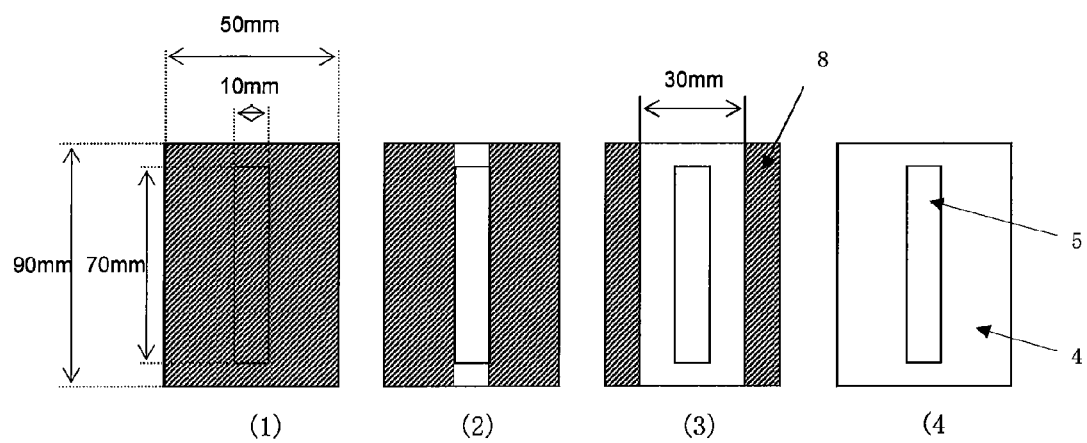
FIG. 6 is a top view showing examples of measuring electric current amount per surface unit area using the acrylic slit plate according to the second embodiment.

Moreover, the relationship between the shape of the cathode electrode 5 attached to the dielectric material and the distribution of discharged amount of electron is also examined. That is, as shown in FIG. 5, the cathode electrode 5 is prepared as a strip (10 mm×70 mm) and closely attached to the center of dielectric material sheet 4 (50 mm×90 mm). A high polymer gel 11 similar to the human arm is placed between the dielectric material sheet 4 and the anode electrode 7. Then, the four different patterns (1) to (4) of 2-mm-thick acrylic slit plate 8 shown in FIG. 6 is disposed between the dielectric material electrode 9 and the high polymer gel 11, and the contact area of the slit with respect to the dielectric material electrode 9 and high polymer gel 11 is increased stepwise. Accordingly, change in the amount of discharged current corresponding to increase in the contact area is measured.

Figures 7, 8:
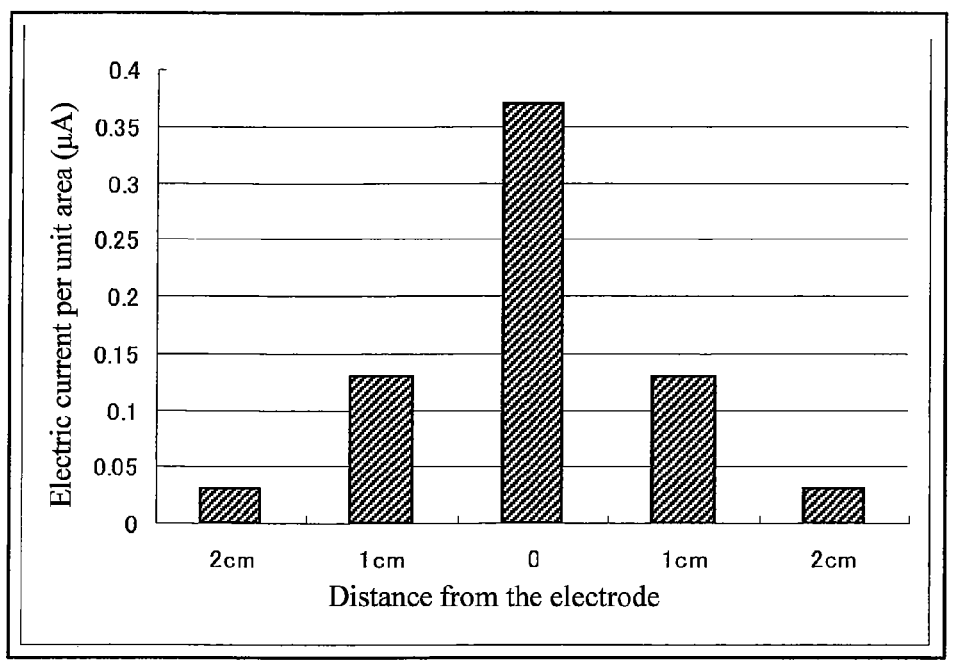
FIG. 7 is a table showing measured values of the electric current per unit area in use of the acrylic slit plate shown in FIG. 6.
FIG. 8 is a graph showing the amount of the electric current per unit area corresponding to the distance from the electrode according to the second embodiment.

FIG. 7 is a table showing the results of measurement. As shown in FIG. 7, the amount of discharged current per unit area becomes the highest in the surface area of dielectric material positioned just below the cathode electrode 5 and contacting therewith. On the other hand, in as the area being distant from the cathode electrode 5, the amount of discharged current per unit area of the dielectric material surface become decreased. Thus, as shown in FIG. 8, the electron was discharged with the gradient of concentration like a normal distribution model. This is schematically shown in FIG. 9.

Figures 9, 10:
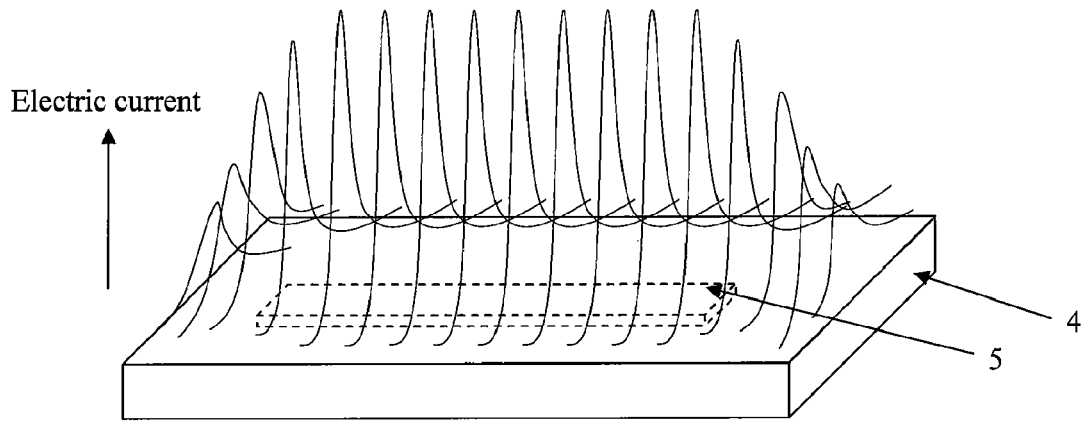
FIG. 9 is a schematic diagram showing the concentration gradient of discharged electron according to the second embodiment.
FIG. 10 is a table showing the measured values of discharged electric current amount per unit area according to the second embodiment of the invention.
Figure 11:
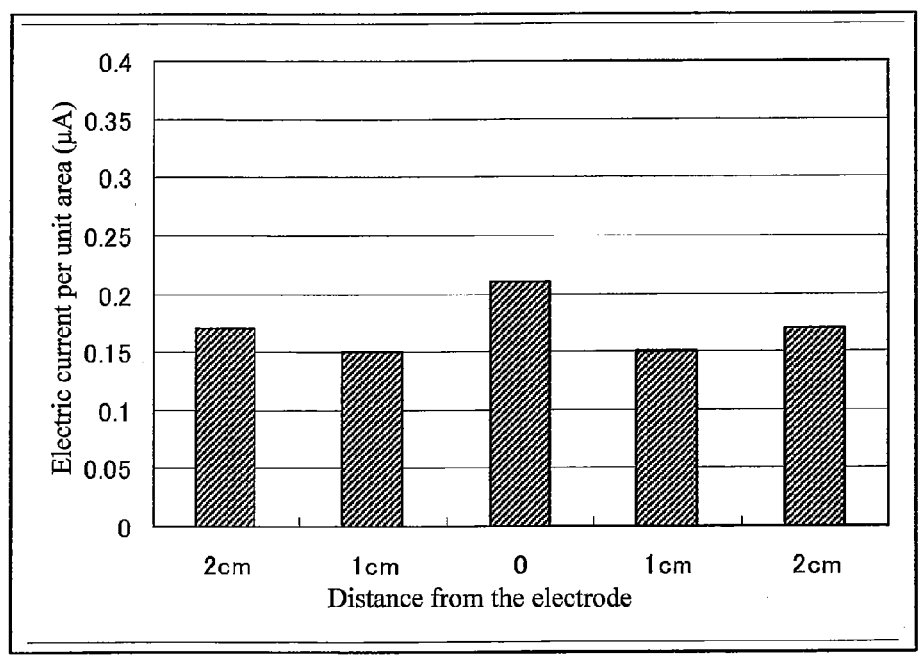
FIG. 11 is a graph showing the amount of the electric current per unit area according to the second embodiment.
Figure 12:
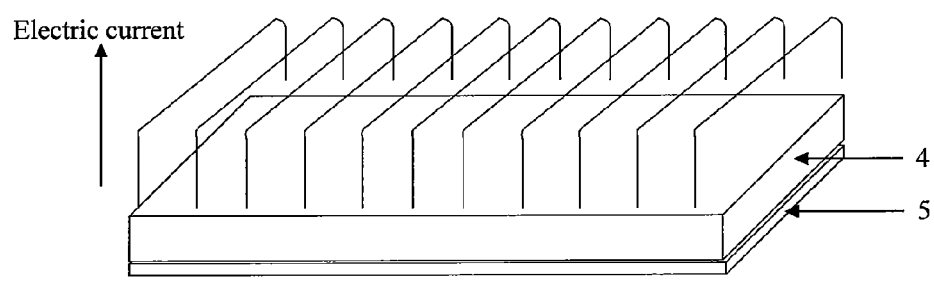
FIG. 12 is a schematic diagram showing the concentration gradient of discharged electron according to the second embodiment.

Also, as shown in FIG. 10 and FIG. 11, when the cathode electrode and dielectric material are made to have the same surface area (50 mm×90 mm) and arranged as one being placed over the other, the discharged current per unit area of the dielectric material surface is almost evenly distributed. This is schematically shown in FIG. 12.

As seen from the above results, by means of the shape and position of the cathode electrode attached to the dielectric material, the concentration gradient of appropriate amount of discharged electron is adjustable on the surface of dielectric material, and under the same power-supply voltage, a necessary amount of electron can be restrictedly irradiated to a necessary region.

Figure 13:
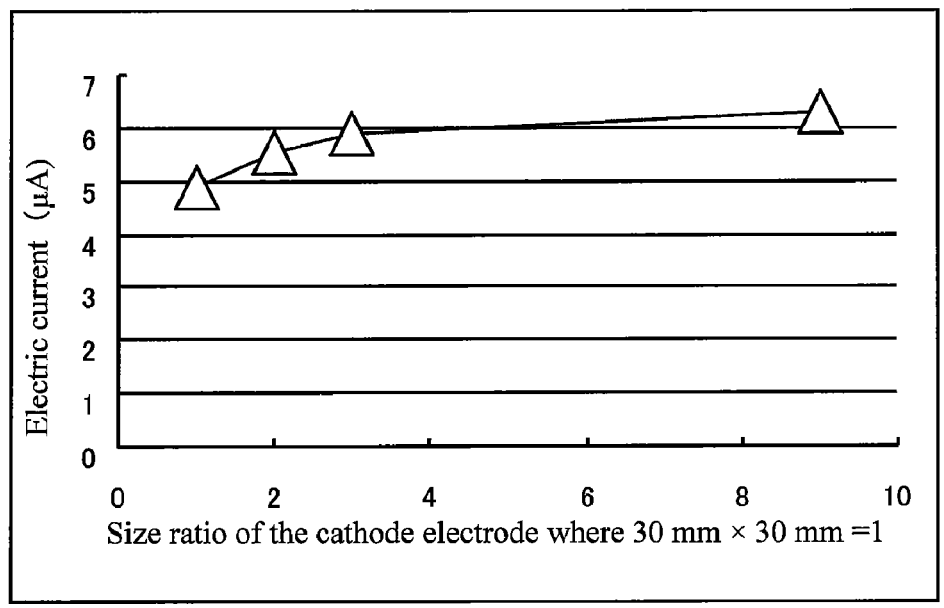
FIG. 13 is a graph showing the relationship between the size of anode electrode and the amount of discharged electron according to the second embodiment.

Furthermore, as shown in FIG. 13, the amount of discharged current from the barrier discharge electrode 9 is influenced also by the area of conductive anode electrode 7 that is opposed to the discharge electrode, and by increasing the area of anode electrode 7, the amount of discharge is increased. In addition, from the fact that the amount of discharge is decreased when the barrier discharge electrode 9 is covered with the insulative cotton cloth, it is found that the area of anode electrode 7 and also the conductivity of material attached to the anode electrode 7 influence the amount of discharge from the dielectric material sheet 4.

As seen from the above first embodiment and second embodiment, it is found that the amount of discharged electron of DC-type dielectric barrier discharge according to the present invention is influenced by the factors listed below:

1. Volume resistivity of the dielectric material
2. Relative permittivity of the dielectric material
3. Thickness of the dielectric material
4. Conductive substance added to the dielectric material
5. Voltage applied to the dielectric material
6. Area of cathode electrode attached to the dielectric material
7. Shape of cathode electrode attached to the dielectric material
8. Area of anode electrode opposed to the dielectric material
9. Conductivity of anode electrode opposed to the dielectric material According to the invention, by preparing the DC-type dielectric barrier discharge electrode in consideration of the above factors for control, it becomes possible to generate planar discharge from the whole area of the dielectric material and allow a unidirectional and constant current to be flowed between the plate electrodes opposed to each other.

(Third Embodiment)

Next, a third embodiment is explained, in which the electron irradiation apparatus with the configuration shown in the first embodiment and second embodiment is applied to an electrical therapeutic apparatus. It is known from more than 100 years ago that a weak electric current given to the human body has a physiologic effect. Recently, the importance of a therapeutic method using a weak current has been pointed out, for example, there is a report that the weak current stimulates wound healing.

In order to safely apply to the human body a weak electron as unidirectional and constant discharged current, the electron irradiation apparatus of the DC-type dielectric barrier discharge shown in the first embodiment and second embodiment are effective. The third embodiment, having a configuration shown in FIG. 14 to FIG. 17, is a specific example of applying the electron irradiation apparatus of the present invention to the electrical therapeutic apparatus.

Figure 14:
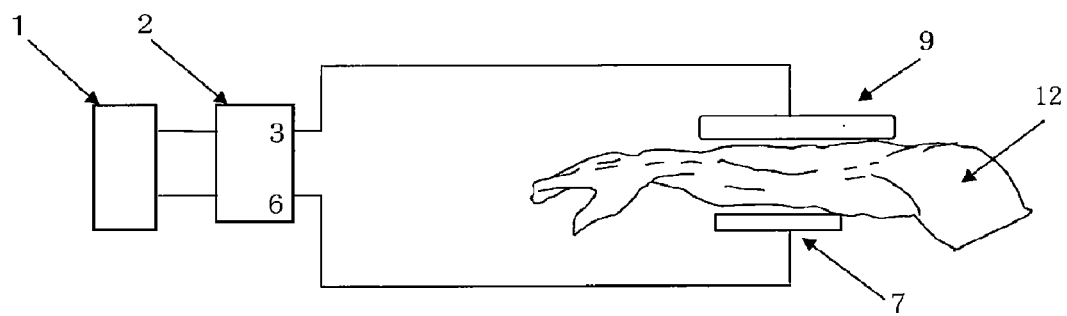
FIG. 14 is a wiring diagram showing a third embodiment of the invention.

As shown in the wiring diagram of FIG. 14, as a drive power supply, a DC power supply 1 using an external dry battery is employed. The DC power supply 1 is connected with the DC-type high voltage generator 2 for boosting, and its negative output terminal 3 at mean negative bias voltage is connected to the cathode electrode 5. As shown in the cross-sectional view of FIG. 15, the cathode electrode 5 and the dielectric material sheet 4 made of polyurethane (90 mm long×50 mm wide×2 mm thick) are closely attached to each other and covered with the insulation cloth 13 so as to compose the dielectric material combined electrode 9. On the other hand, the positive output terminal 6 on the 0 volt side of the DC power supply 1 is connected to the anode electrode 7 covered with an insulation cloth.

Between the pair of electrodes 9 and 7, a portion 12 to be treated in the human body is disposed. By applying the DC high voltage, the DC-type dielectric barrier discharge occurs and the electrons generated by planar discharge is supplied to the human body non-invasively via the contact area on the body.

Figure 15:
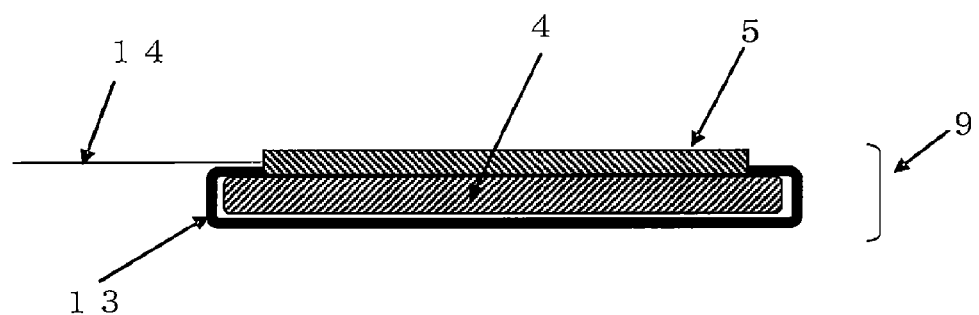
FIG. 15 is a cross-sectional view showing the part of combined electrode for dielectric barrier discharge according to the third embodiment.
Figure 16:
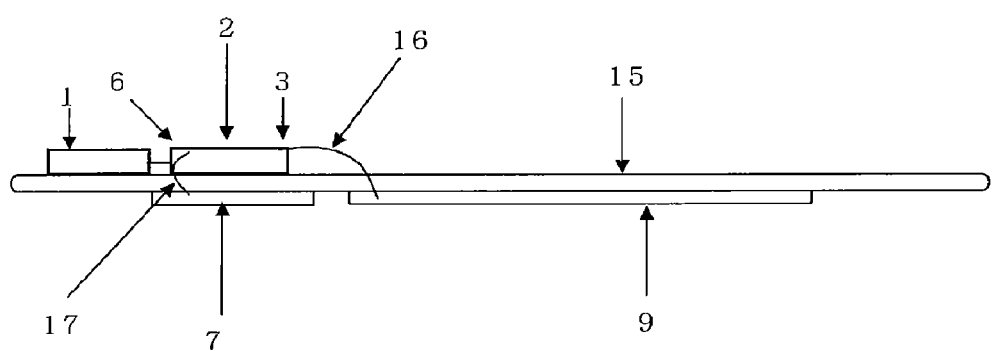
FIG. 16 is a side view showing the whole structure of the third embodiment.
Figure 17:
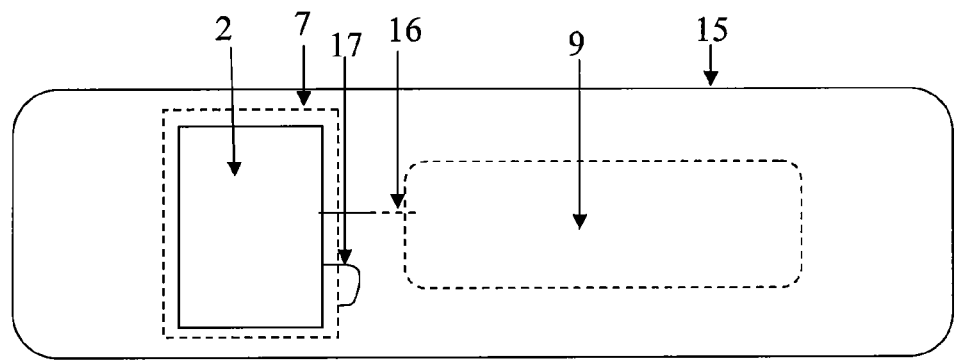
FIG. 17 is a top view according to the third embodiment.

FIGS. 16 and 17 are a side view and a top view, respectively, showing an example in which the electron irradiation apparatus shown in FIGS. 14 and 15 is applied to the mobile-type electrical therapeutic apparatus. As shown in FIG. 16, on the upper surface of a belt-type attachment 15, the drive power supply 1 and DC-type high voltage generator 2 are placed, and, on the lower surface, the discharge electrode 9 and the anode electrode 7 are placed. The negative side output terminal 3 of the DC-type high voltage generator 2 is connected to the discharge electrode 9 via the conductive wire 16, and the positive side output terminal 6 of the DC-type high voltage generator 2 is connected to the anode electrode 7 via the conductive wire 17. In this case, as shown in FIG. 17, DC-type dielectric barrier discharge electrode 9 and anode electrode 7 are located on the same side of the belt-type attachment 15 so that when the attachment 15 is wrapped around the affected part of a subject to be treated, the electrodes 9 and 7 are positioned to be opposed to each other with placing the affected part therebetween.

Figure 18:
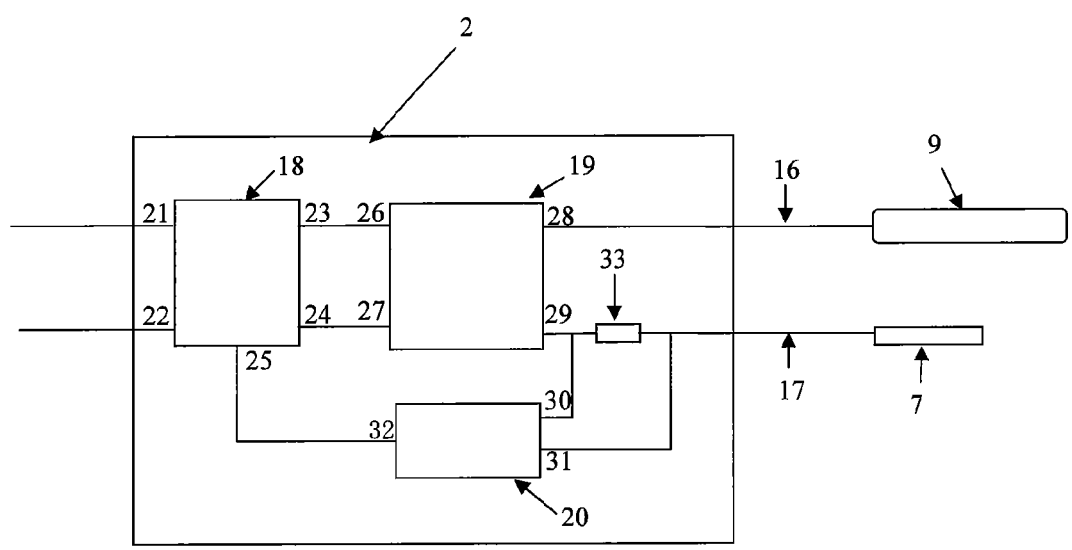
FIG. 18 is a block diagram showing the controlling circuit according to the third embodiment.

Moreover, the amount of discharged current from the dielectric material changes depending on the humidity and temperature of human body surface, therefore, for the use of therapeutic apparatus, it is necessary to have a circuit to control the amount of discharged current within a certain appropriate range. For this purpose, in the third embodiment, as shown in FIG. 18, the DC-type high voltage generator 2 is equipped with a variable voltage power supply circuit 18, a high voltage rectifier circuit 19, and a feedback controlling circuit 20.

That is, the input voltage from the power supply input terminals 21 and 22 of the variable voltage power supply circuit 18 is outputted to the output terminals 23 and 24 corresponding to the input voltage amount from the output terminal 32 of the feedback controlling circuit 20 to the controlled voltage input terminal 25 is outputted to the output terminals 23 and 24. The output voltage of the variable voltage power supply circuit 18 applied from the input terminals 26 and 27 of the high voltage rectifier circuit 19 is converted to a necessary voltage, rectified, and then outputted as a DC voltage from the output terminals 28 and 29.

The feedback controlling circuit 20 detects the voltage at both the terminals of a resistor 33, which is serially inserted in the conductive wire 17 via which the anode electrode 7 is connected to the high voltage rectifier circuit 19. The voltage is inputted to the input terminals 30 and 31 of the feedback controlling circuit 20, and when the voltage at both the terminals of the resistor 33 becomes higher than a reference voltage that is pre-set inside, the circuit decreases the output voltage of the variable voltage supply circuit 18 by outputting the voltage from the output terminal 32. When a level of current flowing through the conductive wire 17 connected to the anode electrode 7 is higher than a pre-set value, the controlled voltage is outputted to the variable voltage supply circuit 18 such that the current does not exceed the value pre-set within the feedback controlling circuit 20. As such, the whole system constitutes the negative feedback circuit.

As explained above, according to the third embodiment, the negative feedback is used such that the current produced by the dielectric barrier discharge does not exceed a certain level. Therefore, it becomes possible to prevent an excess current due to changes in humidity caused by sweating etc. upon wearing on the human body, thereby achieving the safety during the therapy.

The invention claimed is:

1. An electron irradiation apparatus of DC-type dielectric barrier discharge comprising:
   a DC-type high voltage power supply;
   a cathode electrode connected to a negative output terminal of the DC-type high voltage power supply;
   an anode electrode connected to a positive output terminal of the DC-type high voltage power supply; and
   a dielectric material closely attached to a surface of the cathode electrode facing to the anode electrode, the dielectric material together with the cathode electrode constituting a dielectric discharge electrode,
   wherein electrons are discharged unidirectionally from a surface of the dielectric material by applying a DC high voltage between the dielectric discharge electrode and the anode electrode.

2. The electron irradiation apparatus of DC-type dielectric barrier discharge according to claim 1, wherein the dielectric material is made of a substance of which volume resistivity is $10^{13}\,\Omega\cdot\text{cm}$ or less and relative permittivity is 5 or more.

3. The electron irradiation apparatus of DC-type dielectric barrier discharge according to claim 1, wherein the dielectric material is formed by mixing a raw dielectric material with a conductive substance such that the volume resistivity is decreased and the relative permittivity is increased.

4. An electrical therapeutic apparatus equipped with the electron irradiation apparatus according to claim 1, wherein a region to be irradiated is arranged between the dielectric discharge electrode and the anode electrode of the electron irradiation apparatus.

5. The electrical therapeutic apparatus according to claim 4, wherein the electron irradiation apparatus comprises a current controlling circuit to adjust a maximum current flowing between the electrodes at a pre-set current value.

6. The electron irradiation apparatus of DC-type dielectric barrier discharge according to claim 2, wherein the dielectric material is formed by mixing a raw dielectric material with a conductive substance such that the volume resistivity is decreased and the relative permittivity is increased.

7. An electrical therapeutic apparatus equipped with the electron irradiation apparatus according to claim 2, wherein a region to be irradiated is arranged between the dielectric discharge electrode and the anode electrode of the electron irradiation apparatus.

8. An electrical therapeutic apparatus equipped with the electron irradiation apparatus according to claim 3, wherein a region to be irradiated is arranged between the dielectric discharge electrode and the anode electrode of the electron irradiation apparatus.

* * * * *